(12) United States Patent
Ritter (10) Patent No.: US 9,265,873 B2
(45) Date of Patent: Feb. 23, 2016

(54) DIALYSIS DEVICE AND METHOD FOR OPERATING A DIALYSIS DEVICE

(75) Inventor: Kai-Uwe Ritter, Melsungen (DE)

(73) Assignee: B. BRAUN AVITUM AG, Melsungen (DE)

( * ) Notice: Subject to any disclaimer, the term of this patent is extended or adjusted under 35 U.S.C. 154(b) by 303 days.

(21) Appl. No.: 14/003,325

(22) PCT Filed: Jan. 10, 2012

(86) PCT No.: PCT/EP2012/050286
§ 371 (c)(1),
(2), (4) Date: Oct. 2, 2013

(87) PCT Pub. No.: WO2012/119799
PCT Pub. Date: Sep. 13, 2012

(65) Prior Publication Data
US 2014/0014580 A1 Jan. 16, 2014

(30) Foreign Application Priority Data
Mar. 9, 2011 (EP) ..................................... 11157528

(51) Int. Cl.
*A61M 1/16* (2006.01)
*B01D 3/00* (2006.01)
*B01D 5/00* (2006.01)

(52) U.S. Cl.
CPC .................. *A61M 1/16* (2013.01); *A61M 1/166* (2014.02); *A61M 1/1656* (2013.01); *A61M 1/1662* (2014.02); *A61M 1/1664* (2014.02); *A61M 1/1686* (2013.01); *A61M 1/1658* (2013.01); *A61M 2205/3606* (2013.01); *B01D 3/007* (2013.01); *B01D 5/0039* (2013.01); *B01D 2313/38* (2013.01)

(58) Field of Classification Search
CPC ....... A61M 1/14; A61M 1/16; A61M 1/1662; A61M 1/1656; A61M 1/1664; A61M 1/1686; A61M 2205/3606; A61M 1/1658; A61M 1/166; B01D 2313/38; B01D 5/0039; B01D 3/007

See application file for complete search history.

(56) References Cited

U.S. PATENT DOCUMENTS

| 3,515,275 A | 6/1970 | Bowman |
| 3,878,095 A | 4/1975 | Frasier et al. |
| 5,861,555 A | 1/1999 | Hobro et al. |

(Continued)

FOREIGN PATENT DOCUMENTS

| DE | 2 005 808 | 9/1971 |
| EP | 0 428 009 | 5/1991 |
| WO | WO 96/09080 | 3/1996 |

(Continued)

OTHER PUBLICATIONS

International Search Report for PCT/EP2012/050286 mailed Apr. 4, 2012.
European Opposition Notice for EP 2 497 507 mailed Jan. 9, 2015.
Drukker et al., "Replacement of Renal Function by Dialysis," Kluwer Academic Publishers, 1996, Hemodialysis Machines and Monitors, p. 344.

(Continued)

*Primary Examiner* — John Kim
(74) *Attorney, Agent, or Firm* — RatnerPrestia (57) ABSTRACT

A dialysis unit includes both an inlet for guiding dialysis fluid in a direction of flow to a dialyzer membrane and an outlet for discharging dialysate from the dialyzer membrane. A heat pump configured to exchange thermal energy between a heat reservoir and the dialysis fluid in the inlet is coupled to the inlet.

14 Claims, 6 Drawing Sheets

(56) References Cited

U.S. PATENT DOCUMENTS

2003/0212314 A1    11/2003    Takahashi et al.
2009/0038307 A1    2/2009    Smith et al.

FOREIGN PATENT DOCUMENTS

| | | |
|---|---|---|
| WO | WO 2007/120812 | 10/2007 |
| WO | WO 2010/040819 | 4/2010 |

OTHER PUBLICATIONS

Gerthsen et al., "Physik ein Lehrbuch zum Gebrach neben Vorlesungen," Springer Verlag Berlin Heidelberg New York Tokyo, revised and extended by H. Vogel, 1986, Ch. 5, p. 210, with translation.

"Ground Source Heat Pump: A guide book," EGEC, 2008.

Statement regarding EP 2 497 507 by Fresenius Medical Care AG & Co. KGaA dated Nov. 19, 2014, with translation.

DIALYSIS DEVICE AND METHOD FOR OPERATING A DIALYSIS DEVICE

CROSS REFERENCE TO RELATED APPLICATIONS

This application is the U.S. national phase application of PCT International Application No. PCT/EP2012/050286 filed Jan. 10, 2012, which claims priority to European Application No. 11 157 528.8 filed Mar. 9, 2011, the contents of each application being incorporated by reference herein.

FIELD OF THE INVENTION

The present invention deals with a dialysis unit and a procedure of operating a dialysis unit.

BACKGROUND INFORMATION

Dialysis is a blood purification procedure used in the case of renal failure as a replacement method. Apart from renal transplantation, dialysis is the most important renal replacement therapy in the case of chronic renal failure and one of the possible alternative treatments in the case of acute renal failure. It is the aim of dialysis to keep the concentration of substances that are usually eliminated with the urine or are pathogenic, as the case may be, in the blood and/or in the body of the patient below a toxic limit.

Blood purifying therapy procedures are based on the physical basic principles of diffusion, osmosis and convection and partly also adsorption. The different procedures of dialysis are usually based on exchange of substance via specific semipermeable membranes hereinafter referred to as dialyser membranes. Inter alia, dialysis causes the purification of the blood, the removal of water from the blood circulation and the addition of electrolytes to the blood. In dialysis on one side of the dialyser membrane there is provided blood or blood plasma and on the other side of the membrane there is a dialysis solution or a dialysis fluid, respectively. Depending on the nature of the membrane, different substances diffuse through the membrane from the blood into the dialysis fluid and in this way are removed from the blood circulation. At the same time, other substances such as electrolytes can also diffuse from the dialysis fluid into the blood. One of the crucial parameters is the nature of the membrane and especially the pore size thereof substantially determining which substances are removed from the blood during dialysis. The use of such semipermeable membranes therefore is also referred to as selective diffusion. While the membrane substantially determines the type and the size of the basically exchangeable substances, the diffusion rate and thus the actual exchange is substantially determined by the differences in concentration of the respective substances on the different sides of the membrane. The substances to be removed are roughly classified into low-molecular, medium-molecular and high-molecular substances. Moreover, the water balance of the patient can be controlled by osmosis or a pressure difference artificially produced between the different sides of the dialyser membrane by liquid being removed from the blood to be purified. In addition, specific additives in the dialysis fluid are adapted to influence and regulate the acid-base state and the electrolyte composition of the blood.

The dialyser membranes used are, on the one hand, artificial or technical membranes, but on the other hand also endogenous physiological membranes. Hence in dialysis a distinction is made between extracorporeal procedures using artificial membranes outside the body and intracorporeal procedures performed inside the body and making use of endogenous membranes.

An example of an intracorporeal dialysis procedure is constituted by the peritoneal dialysis in which the peritoneum is used as membrane for blood purification. In this case the dialysis fluid is directly introduced through a catheter port into the peritoneal cavity of the patient and is exchanged as dialysate after completed equilibration of the substance concentrations. Typically, in this way three to six exchanges of the dialysis fluid, distributed over one day, having a volume of about 2.5 to 4 liters each are performed. In order to avoid negative health consequences for the patient, the dialysis fluid has to be brought to body temperature each time before being introduced into the peritoneal cavity.

An example of an extracorporeal dialysis procedure is the hemodialysis applied most all over the world. This procedure pursues the principle of concentration balance of small-molecular substances of two fluids which are separated outside the body in a dialyser by an artificial semipermeable dialyser membrane. Being separated by the dialyser membrane, on the one side the blood including nephrotoxins, electrolytes such as potassium and phosphate as well as substances usually eliminated with the urine is provided. On the other side of the dialyser membrane a low-germ processed solution is provided as dialysis fluid which contains no waste products and includes a share of electrolytes oriented at the respective needs of the patient. The semipermeable dialyser membrane between blood and dialysis solution or dialysis fluid, resp., has pores allowing small molecules such as water, electrolytes and substances usually eliminated with the urine (e.g. urea, uric acid) to pass but withholding large molecules such as proteins and blood cells.

In the procedure of hemodialysis three to four treatments for about 4 h per week are typical. For each treatment a considerable amount of dialysis fluid is required which permanently bypasses the membrane on the side of the dialyser membrane facing away from the blood. Frequently, the dialysis fluid is guided to the blood in a counter-current. The dialysis fluid is discharged as dialysate after single use when enriched with substances usually eliminated with the urine. In general, for reasons of unambiguous assignment, the fluid used for dialysis is referred to as dialysis fluid prior to being enriched with substances usually eliminated with the urine, whereas the fluid enriched with the substances usually eliminated with the urine is referred to as dialysate. The quantity of dialysis fluid consumed can amount to 100 l and more for each application. Solely the large quantity of dialysis fluid to be produced and consumed renders a dialysis treatment extremely costly. In addition to the high consumption of resources, the energy consumed to process the dialysis fluid considerably increases the costs.

Apart from the quantity of the fluid supplied and/or withdrawn from the blood, also the temperature of the blood has to be exactly controlled so as to prevent serious damage to the patient. The blood supplied to the patient again after its purification must have a temperature dependent on the body temperature of the patient so as to avoid such damage to the health. This is obtained by heating the dialysis fluid and thus also the dialyser membrane and the components surrounding said membrane to body temperature so as to prevent the blood from cooling in the extracorporeal circulation.

Before the dialysis fluid is passed by the blood of the patient by means of a dialysis unit in a dialyser including the filter membrane, it is thus heated from the input temperature (typically 10° C.) to a higher temperature approximately at the level of the blood temperature (typically 36° C.). When the dialysate has flown through the dialysis filter, it is used up and is discharged in the outlet. Said tempering of the large quantity of dialysis fluid consumes a considerable amount of additional energy.

In the extracorporeal methods such as hemodialysis (HD) moreover after each dialysis treatment the apparatus used, i.e. the dialyser, should be sterilized in order to prevent cross-infection between individual patients. For this purpose, the so called hot disinfection is frequently applied. In this case a water/disinfectant mixture is heated in the dialysate circulation of the dialyser to >85° C. and is circulated for a particular time, typically about 15 minutes. After expiry of this period of time, the disinfectant should be rinsed out as quickly as possible and the machine or the dialyser, as the case may be, as quickly as possible should be cooled to approx. 35° again so as to enable the next therapy.

As further extracorporeal dialysis procedures hemofiltration or hemodiafiltration are mentioned by way of example only which partly consume even higher amounts of resources and energy and therefore incur similar or higher costs when being applied.

Due to the high consumption of resources and the high energy consumption for a dialysis treatment, there is a considerable need to render dialysis units and procedures for operating dialysis units more efficient.

SUMMARY OF THE INVENTION

In several embodiments of dialysis units a heat pump is coupled to an inlet means serving for guiding a dialysis fluid to a dialyser membrane so as to exchange thermal energy between a heat reservoir and the dialysis fluid in the inlet means. This can result in considerable reduction of the energy consumption and considerable increase in the efficiency when temperature controlling the dialysis fluid and thus in an increase in the efficiency of the dialysis unit.

In several embodiments the heat pump is used to heat the dialysis fluid in the inlet means. By using a heat pump which, compared to other heating options such as an electric direct heating, exhibits a considerably higher efficiency, the energy required to operate a dialyser can be considerably reduced. The higher efficiency when using a heat pump is due to the fact that the thermal energy output by the heat pump to the dialysis fluid is higher than the energy required to operate the heat pump, because the heat pump transfers the thermal energy from the heat reservoir to the dialysis fluid instead of generating it on its own. Thus the heat pump is superior both to other heating systems directly converting primary energy carriers into thermal energy and to conventional electric heating systems.

In several further embodiments an ambient medium such as the ambient air is used as heat reservoir. The increase in efficiency to be gained when using a heat pump, which is derived from Carnot's procedure, is dependent on the difference in temperature between the two mediums coupled by the heat pump, hence in the present case the temperature of the heat reservoir and the temperature of the dialysis fluid. This factor also referred to as coefficient of performance (COP) becomes higher, the higher the temperature of the heat reservoir relative to the temperature of the dialysis fluid. For instance, in southern countries a heat pump in the inlet means of a dialyser can heat the dialysis fluid in an especially efficient way, when the ambient air is used as heat reservoir. At the same time, when employing such heat pump the ambient air is cooled so that, apart from the required functionality for the dialyser, it can also bring about a comfortable climate for the patient.

In further embodiments the heat pump is additionally coupled to an outlet means of the dialysis unit which is used to discharge the already used dialysate from the dialyser membrane. The dialysate can be used as heat reservoir in the outlet means.

In these embodiments, in a first operating mode the already used dialysate which is preheated and thereby has approximately body temperature can be used to serve as heat reservoir or as heat source, respectively, for the heat pump. That is to say, the energy already used to heat the consumed dialysate can be recovered in large parts to heat the fresh dialysis fluid in the inlet means. This results in a further considerable reduction of the energy consumption during dialysis, i.e. altogether in an increase in the efficiency when operating a dialysis unit/apparatus. The efficiency of heat recovery by means of a heat pump for the afore-mentioned reasons is considerably higher than the efficiency of a conventional heat exchanger, for example.

Although in several embodiments the heat reservoir has a higher temperature than the dialysis fluid, the term heat reservoir is not meant to be dependent on a temperature in any way here and in the following. Each energy reservoir or medium from which thermal energy can be withdrawn or to which thermal energy can be supplied is understood to be a heat reservoir.

In a second operating mode, further embodiments of dialysis units/apparatuses allow to transfer thermal energy from a fluid in the inlet means to the heat reservoir in order to cool the dialysis fluid or a rinsing fluid in the inlet means. In this operating mode the dialysate or another fluid, for example, can be used in the outlet means as a heat sink. This can considerably reduce a period of time required by a dialyser after hot disinfection for cooling to an operating temperature comparable to the body temperature, as a rinsing fluid is actively cooled in the inlet means. Thereby both the fluid quantity required for rinsing and the rinsing time is reduced, which altogether results in an increase in the efficiency during operation of a dialysis unit/apparatus.

In several embodiments an extra heating device is additionally coupled to the inlet means in a flow direction of the dialysis fluid between the heat pump and the dialyser membrane so as to heat the inflowing still non-used dialysis fluid. This can contribute to accelerated heating of the dialysis fluid at the start of operation of the dialysis unit, when the dialysate in the outlet means has not yet reached the desired operating temperature. Such extra heating device can be an electric heating, for instance, and can be dimensioned to be significantly smaller than in a dialysis unit that is solely provided with a conventional heating device, because the extra heating means has only a backup function in this case.

In several embodiments the extra heating device is employed to perform fine adjustment of the temperature of the dialysis fluid in the inlet means. This can be used to ensure that the temperature of the dialysis fluid is within a required temperature window at any point in time. In several embodiments the extra heating device can also be used during cleaning the dialysis unit to heat a fluid used for cleaning to a higher temperature than the dialysis fluid during dialysis.

Several embodiments further include a degassing device coupled to the inlet means which serves for removing gases or air bubbles dissolved in the dialysis fluid. In several embodiments the heat pump is arranged in the flow direction of the dialysis fluid behind the degassing device so as not to additionally heat the components of the degassing device. This entails another increase in efficiency of the dialysis unit.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
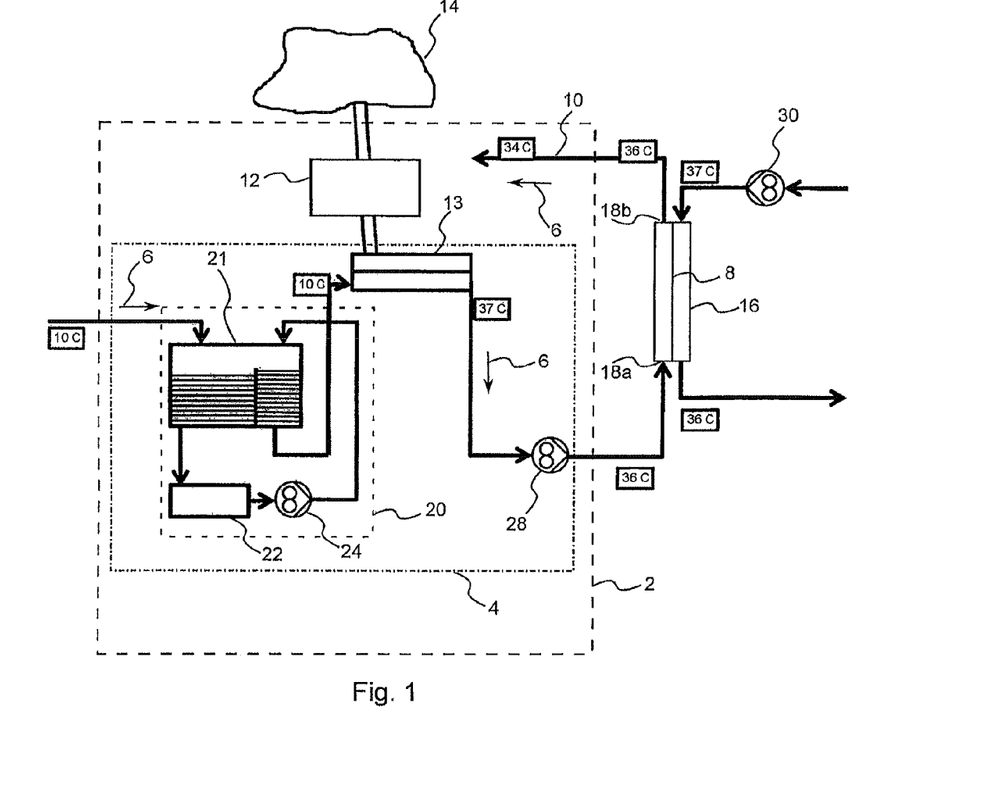
FIG. 1 an embodiment of a dialyser comprising a heat pump.

FIG. 1 illustrates an embodiment of a dialysis unit 2 having an inlet 4 so as to guide a dialysis fluid in a direction of flow 6 to a dialyser membrane 8. The dialysis unit 2 further comprises an outlet 10 for discharging a dialysate from the dialyser membrane 8. A heat pump 12 designed to exchange thermal energy between a heat reservoir 14 and the dialysis fluid in the inlet 4 is coupled to the inlet 4.

By the outlet 10 in the present case all devices or lines, are understood in which the dialysate can be guided or transported in the direction of flow 6 shown in FIG. 1 after the process of dialysis inside the dialyser 2 itself. Equally, by the inlet 4 of the dialysis unit 2 any device or line inside the dialysis unit 2 is understood which is or can be used to guide dialysis fluid or components of a dialysis fluid to the dialyser membrane 8. Consequently, by the inlet 4 especially also a tubing system or one or more devices guiding or processing the dialysis fluid are to be understood.

As is shown in FIG. 1, the dialyser membrane 8 or a dialyser 16 including the dialyser membrane 8 according to some embodiments is no part of the dialysis unit 2. Rather, the dialyser 16 can be exchanged together with the dialyser membrane 8 after each treatment so that no cross infection can occur in the subsequent treatment of another patient. The dialyser 16 includes ports 18a and 18b to couple the inlet 4 and the outlet 10 of the dialysis unit 2 to the dialyser 16 so that the dialysis fluid is guided on one side (on the left in FIG. 1) of the dialyser membrane 8 through the dialyser casing 16.

In order to pass the blood of the patient by the other side (on the right in FIG. 1) of the dialyser membrane 8 a further blood circulation, mentioned here for the sake of completeness only, is required which may comprise a blood delivery pump 30 in particular in the case of a venovenous access to the patient, as shown in FIG. 1.

The heat pump 12 is coupled to the inlet 4, as is shown in FIG. 1, so that thermal energy can be exchanged between a heat reservoir 14 and the dialysis fluid in the inlet 4 by means of the heat pump 12. The medium additionally required for such exchange of thermal energy by means of a heat pump 12 which forms the heat reservoir is represented only schematically in FIG. 1. Although in the embodiment shown in FIG. 1 just as in the embodiments described hereinafter the heat pump 12 is coupled to the dialysis fluid in the inlet 4 by means of a heat exchanger 13, in further embodiments it can be coupled to the inlet 4 also in a different way so as to exchange thermal energy with the inlet 4 or the dialysis fluid or any other fluid in the inlet 4. This can be the case by means of radiation, for example.

As a further optional component, the dialysis unit 2 shown in FIG. 1 shows a degassing device 20 being composed of a fluid reservoir 21, a degassing means 22 and a circulation pump 24. The circulation inside the degassing device 20 schematically represented in FIG. 1 serves for degassing the dialysis fluid, for which purpose the latter is initially guided from a first partial reservoir inside the fluid reservoir 21 via the degassing means 22 into a second partial reservoir. For this purpose, in the embodiment shown in FIG. 1 a delivery pump 24 which drives said partial circulation for degassing is provided.

After the degassing device 20 arranged in the flow direction 6 ahead of the heat pump 12 the degassed dialysis fluid is passed by the position at which the heat pump 12 is coupled to the inlet 4. The heat pump 12 serves for heating the dialysate in the inlet 4 during dialysis so that the dialysate has at least approximately body temperature when it reaches the dialyser membrane 8. In order to maintain the circulation of the dialysis fluid and the dialysate the embodiment shown in FIG. 1 furthermore includes another optional delivery pump 28 transporting the dialysis fluid after being heated by means of the heat pump 12 in the direction of the dialyser membrane 8.

FIG. 1 exemplifies typical temperatures of the dialysis fluid and of the dialysate before and after heating, respectively. For example, the supplied fluid or dialysis fluid can be supplied at a temperature of about 10° C. Before it flows through the external dialyser 16, in the embodiment shown in FIG. 1 the temperature is increased to approx. 37° C. This is done by the heat pump 12 which withdraws a thermal energy required for this purpose from the heat reservoir 14.

It is understood that in this case as well as in the embodiments discussed hereinafter the exact position of the coupling of the individual components to the inlet 4 and/or the position thereof inside the inlet 4 can be exchanged in any way. For example, the degassing device 20 can also be arranged in the flow direction 6 between a coupling position of the heat pump 12 and the dialyser membrane 8 or between the heat pump 12 and the delivery pump 28. As a matter of course, also the given temperatures are meant to be examples only; any other temperatures are also possible. In particular in warm countries or at warm seasons the temperature of the water or the dialysis fluid fed can also be definitely higher than 10° C. at the beginning of the inlet 4 so that the ambient air, for instance, can be used as heat reservoir 14.

Figure 2:
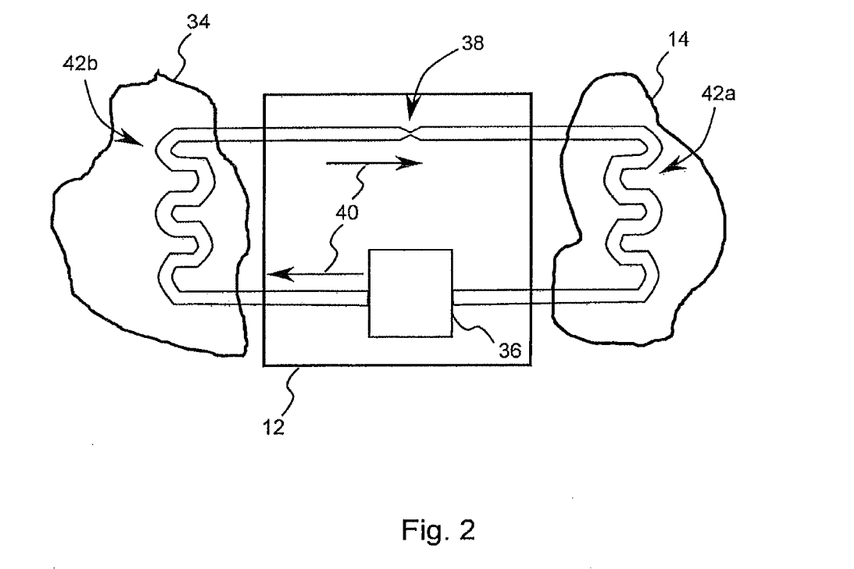
FIG. 2 a schematic diagram of a heat pump.

By way of FIG. 2 the functioning of the heat pump 12 is briefly illustrated for a better understanding of the heat transport between the heat reservoir 14 and the inlet 4.

The heat pump 12 is a machine which pumps heat from a heat source or a heat reservoir 14, resp., to a medium 34 to be heated while supplying technical work. The heat pump was developed to pump thermal energy from a lower to a higher temperature level so that the thermal energy contained in the lower temperature-controlled medium can be used for additionally heating a medium at a higher temperature, which would not be possible by means of usual heat exchangers.

In the case of a heat pump heating the liquefying heat provided at a high temperature level of a working medium used in a heat pump circulation is utilized for heating. On the other hand, in a refrigerating machine the cooling of a refrigerant during expansion and evaporation is used to cool a fluid. Heat pumps and refrigerating machines merely differ regarding the energy used, the heating capacity used either for cooling or for heating. The basic process shown in FIG. 2 is the same, however.

The heat pump 12 shown in FIG. 2 includes a compressor or liquefier 36, resp., and an evaporator or an expansion valve 38, respectively. A working medium frequently also referred to as refrigerant circulates in a circulation means 40 inside a circulation driven by the compressor 36. The compressor 36 can be driven electrically or by an internal combustion engine, for example, and causes the working medium to circulate within the circulation. The compressor 36 compresses the working medium or the refrigerant, resp., to a higher pressure, wherein the working medium, which is usually gaseous ahead of the compressor 36, is heated and subsequently condenses. The energy released upon condensation of the refrigerant is transferred to the medium 34 to be heated in a heat transfer means 42b. For example a heat exchanger can be employed as heat transfer means 42b. Alternatively, the heat can also be transferred to the medium to be heated by other mechanisms, for instance by radiation. Generally speaking, the heat pump 12 or the working medium, respectively, is coupled to the medium 34 to be heated in the embodiments of the invention so that an exchange of thermal energy is possible.

After transferring the thermal energy the working medium or refrigerant, resp., is expanded at a decompressor or an expansion valve 38, where it cools down. The cold refrigerant is then supplied to an evaporator 42a (water-heat exchanger, borehole heat exchanger, air evaporator) and is transformed into the gaseous state by absorbing ambient heat (energy) from the heat source or from the heat reservoir 14, respectively. Concerning the coupling of the evaporator to the heat reservoir 14 the remarks made in the foregoing on the coupling to the medium 34 to be heated apply mutatis mutandis.

The ratio of useful heating capacity to electrical capacity supplied is referred to as COP (coefficient of performance) of the heat pump in specialized literature. The COP has a theoretical maximum value that depends on the temperatures of the heat reservoir 14 and the medium to be heated 34 and can be derived from Carnot's procedure (named after Nicolas Léonard Sadi Carnot).

In the case of typical temperatures the COP has a value of 8 or more. Values that can be currently obtained in practice are comprised between 4 and 6. This means that 4 to 6 times of the energy required for driving the heat pump 12 are transferred to the medium 34 to be heated. When using the heat pump 12 in the dialysis units of the FIGS. 3 and 4, where, unlike the common operating mode of the heat pump 12, thermal energy is transmitted from a higher-temperature reservoir to a lower-temperature medium, the practically obtained values are even higher because of this fact.

Assuming, for example, that the dialysis fluid has to be heated in the inlet 4 from 10° C. to about 36° C. and approx. 120 l are required for one treatment, this results in a required thermal energy of about 3.6 kWh, if it is assumed in an idealizing way that the thermal energy could be generated during heating from another energy source free of losses, which is not the case in reality, of course.

Even when a heat exchanger is employed between the dialysate in the outlet 10 and the dialysis fluid in the inlet 4, only a small part of the energy used can be recovered. Efficiencies for excellent heat exchangers are typically less than 60%-70%, wherein a transfer of thermal energy can only take place as long as the dialysate in the outlet 10 is still warmer than the dialysis fluid in the inlet 4. This is no limiting factor when using a heat pump. Even if an excellent heat exchanger is assumed, for a conventional dialysis unit a minimum energy demand of approx. 1.80 kWh is still resulting to heat the dialysis fluid for a typical treatment.

This energy demand can be considerably reduced when using a heat pump. Assuming that the entire energy used for initially heating the dialysis fluid in the inlet 4 would be transferred from the dialysate in the outlet 10 by means of a heat pump to the dialysis fluid in the inlet 4 so that the dialysate in the outlet 10 would have approximately the same temperature as the dialysis fluid in the inlet 4 prior to heating, even with a minimum COP of 4 to be expected an energy saving of 50% is resulting already, because only one fourth of the thermal energy transferred has to be used as energy for driving the heat pump. In the idealized example, the energy demand can thus be reduced to less than 0.9 kWh. Taking the actually occurring additional losses in conventional dialysis units into account, the obtainable increase in efficiency can be significantly higher.

Figure 3:
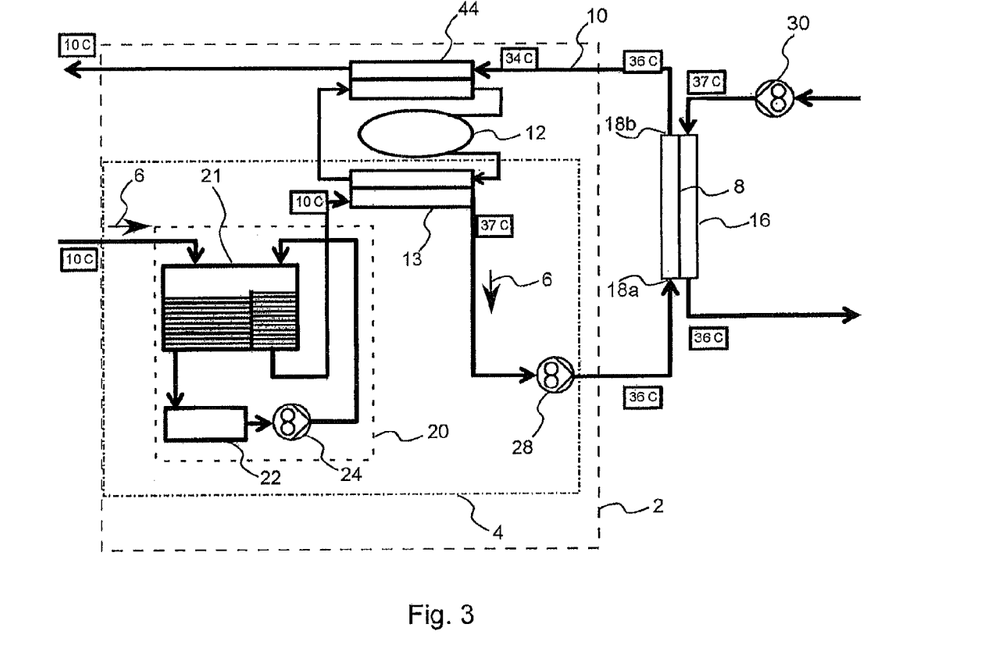
FIG. 3 another embodiment of a dialyser in which a dialysate is used as heat reservoir in the outlet.

FIG. 3 shows another embodiment of a dialysis unit 2 having several components in common with the embodiment illustrated by way of FIG. 1. Therefore, hereinafter only the differences from the embodiment shown in FIG. 1 will be discussed in detail. In general, components having similar or equal functions are provided with the same reference numerals in the embodiments described here. The components described by way of the different embodiments and the functionality thereof moreover can be freely exchanged within the individual embodiments.

In the embodiment shown in FIG. 3 the heat pump 12 utilizes the dialysate in the outlet 10 as heat reservoir. For this purpose, the heat pump 12 is coupled, for instance by means of a heat exchanger 44, to the dialysate in the outlet 10 so that the outflowing dialysate can be used as heat reservoir. During dialysis (the first operating mode of the heat pump in FIG. 3) the compressor 36 contained in the heat pump 12 circulates the working medium of the heat pump 12 in the direction indicated in FIG. 3 so as to transfer thermal energy from the dialysate in the outlet 10 to the dialysis fluid in the inlet 4. Since the procedure leading to the transfer of the thermal energy in the heat pump 12 is reversible, in a second operating mode in which the working medium circulates in the opposite direction the heat pump 12 can also transfer thermal energy from the dialysis fluid or a fluid in the inlet 4 to the dialysate or the fluid in the outlet 10.

Said second operating mode can be of great benefit during or after cleaning a dialysis unit. During the rinsing phase at the end of the hot disinfection the dialysis unit is to reach a temperature of <40° C. as quickly as possible so that the next treatment can be started. The hot disinfection is carried out with hot water of >85° C. to which disinfectant has been added. If a heat exchanger was used for energy recovery, during rinsing of the dialysis unit after disinfection the inflowing fresh water would be heated by the heat exchanger, which is undesired as the rinsing phase is extended. This reduction of efficiency is avoided when a heat pump is employed. When implementing the afore-described second operating mode, a fluid can even be actively cooled in the inlet 4, which entails further increase in efficiency.

Irrespective thereof, the use of a heat pump also during the dialysis procedure has the advantage that the temperature of the dialysate exiting the outlet 10 is lower than this is usually the case. This is very advantageous in hospitals, because thus growth of germs in the outlet is promoted less than this is the case when the outflowing dialysate has a temperature of 20° C. or more.

Figure 4:
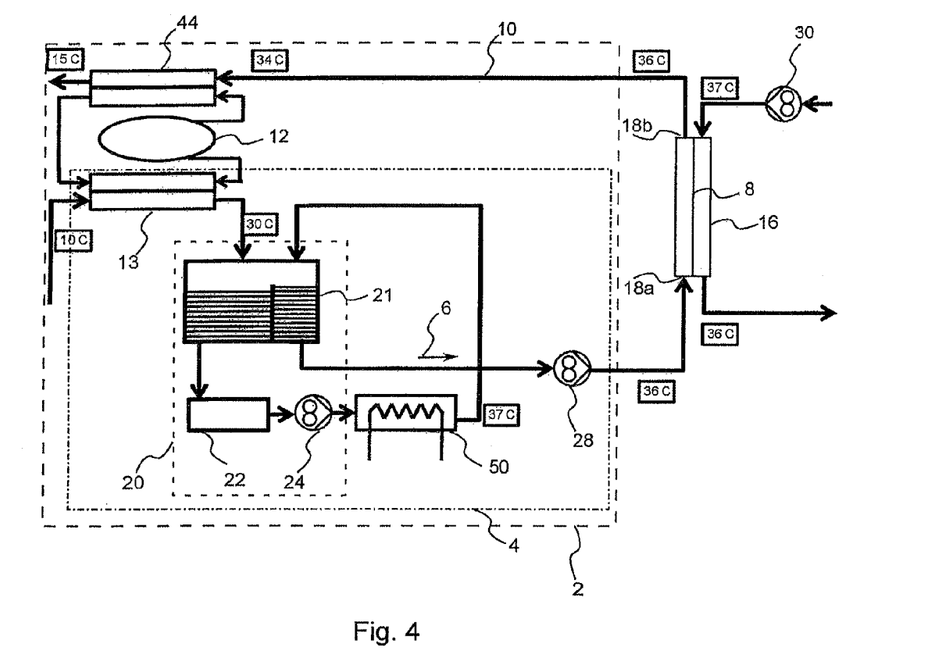
FIG. 4 another embodiment of a dialyser comprising an extra heating means.

FIG. 4 illustrates another embodiment of a dialysis unit in which an extra heating means 50 is additionally coupled to the inlet 4 so as to heat the dialysis fluid in the inlet 4. In the embodiment shown in FIG. 4 the extra heating means 50 is arranged in the direction of flow 6 between the heat pump 12 and the dialyser membrane 8 for heating the dialysis fluid in the inlet 4 additionally and independently of the heat pump 12. When taking the dialysis unit into operation, this can be used to reduce the time required for heating the dialysis fluid to the required temperature, when at the start the dialysate in the outlet 10 does not yet have the temperature obtained in stationary operation. Furthermore, in several embodiments the use of e.g. an electrical heating or a fast-control type heating as extra heating means 50 can ensure that at any point in time the temperature of the dialysis fluid is within a required temperature window.

It is understood that the extra heating means 50 can be coupled at any position to the inlet 4 so as to heat the dialysis fluid in the inlet 4. For example, the extra heating means 50 can also be arranged between the delivery pump 28 and the dialyser membrane 8. In particular, the extra heating means 50 can also be arranged outside the circulation of the degassing device 20.

In other words, FIG. 4 illustrates an embodiment in which a heat pump 12 is utilized to yield the main heat output of the dialysis unit. A small heating is provided to obtain an exact control of the temperature. The amount of inflowing water or dialysis fluid and outflowing dialysate is largely identical. This means that when the heat from the waste water can be made available to the inlet 4 via the heat pump 12, the differential energy to be supplied only has to be the losses resulting from convection or radiation. The heat pump 12 withdraws the energy from the outflowing and consumed dialysate as far as possible in the evaporator on the outlet side. The heat pump 12 compresses the refrigerant. On the other side of the heat circulation of the heat pump 12 a condenser is arranged in the water inlet. There the energy is output to the inflowing water or the inflowing dialysis fluid by condensation. Hence the heat pump 12 heats the inflowing dialysis fluid by the energy withdrawn from the outlet. The temperature of the outflowing dialysate can even be lower than that of the inflowing water.

The heating or extra heating means 50 can accelerate the heating phase at the start of the treatment when the water or the dialysate in the outlet 10 does not yet have an operating temperature. The heating can further serve for increasing the temperature control accuracy. This is only one possible embodiment, however. Also a mixing valve or the like could be used for temperature control.

Summing up, it can be noted that several embodiments of the invention offer one or more of the following advantages:
  The energy efficiency of the machine is increased, because more than the energy supplied during heating can be extracted from the outflowing dialysate.
  Cooling after disinfection is possible. The heat pump 12 can be configured so that during the cooling phase it works in the reversing duty or is switched off, both of which accelerates cooling.
  The outflowing dialysate can be colder than in conventional methods. This can be favorable to reduce the growth of germs in the outlet system.

Figure 5:
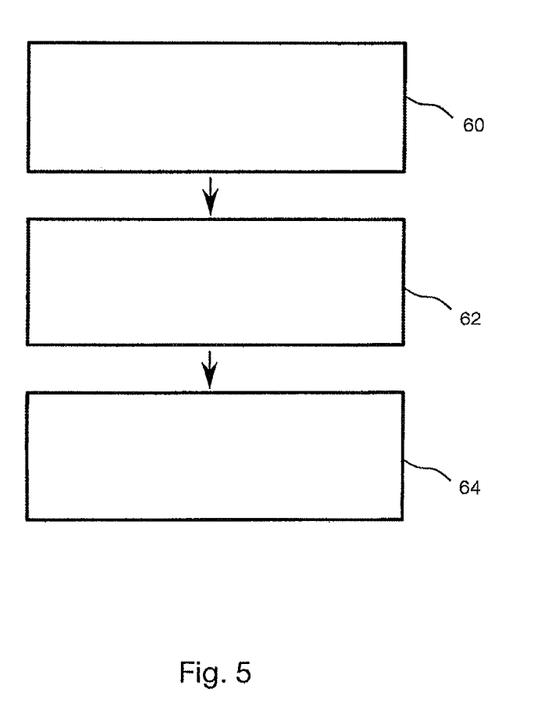
FIG. 5 an example of a procedure for operating a dialyser.

FIG. 5 illustrates an example of a procedure for efficient operation of a dialysis unit.

During supply 60 a dialysis fluid is supplied to a dialyser membrane 8 via an inlet 4. During discharge 62 a dialysate is discharged from the dialyser membrane 8 via an outlet 10. During temperature control 64 the dialysis fluid supplied to the dialyser membrane is temperature-controlled by a heating pump 12.

Figure 6:
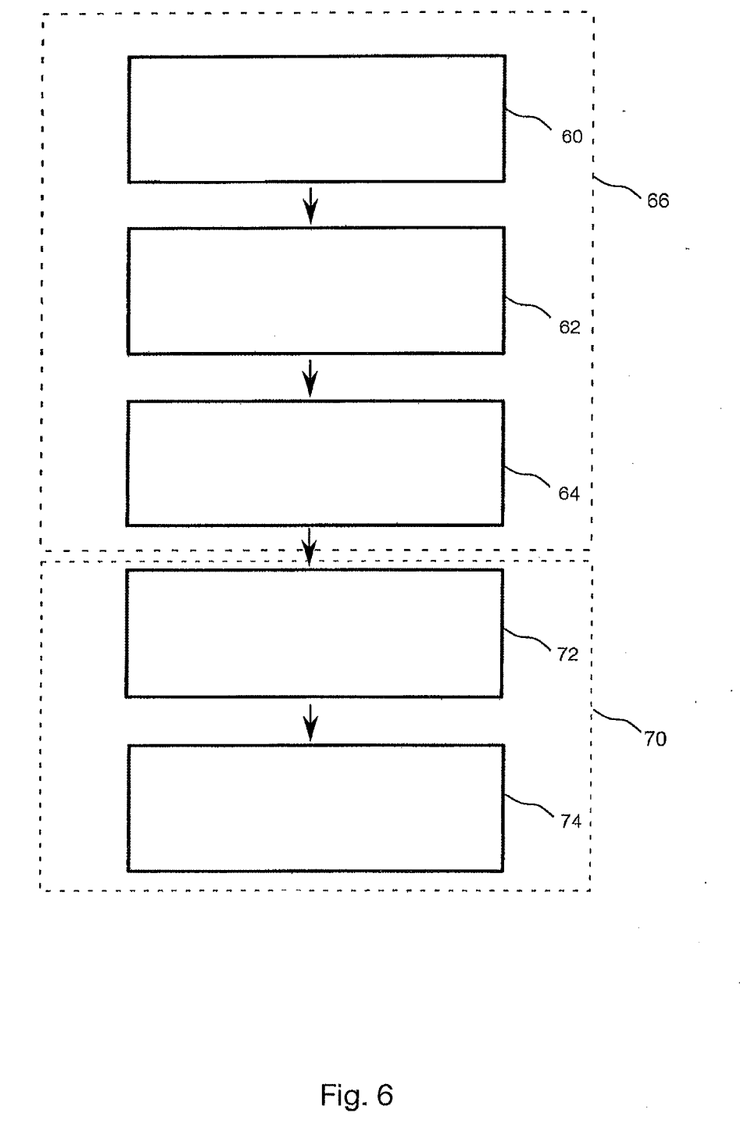
FIG. 6 another example of a procedure for operating a dialysis unit.

FIG. 6 shows another example of a procedure for efficient operation of a dialysis unit which in a first operating mode 66 comprises the steps of the procedure illustrated in FIG. 5, the dialysis fluid supplied to the dialyser membrane 8 being heated by the heat pump 12.

In an optional second cleaning mode 70 the inlet 4 and the outlet 10 are cleaned during cleaning 72 with a cleaning liquid flowing through the inlet 4 and the outlet 10.

During rinsing 74 the dialysis unit a rinsing fluid or the dialysis fluid is cooled in the inlet 4 by means of the heat pump 12 operating in a second operating mode.

The invention claimed is:

1. A dialysis unit comprising the following features:
  an inlet means for guiding a dialysis fluid in a direction of flow to a dialyzer membrane;
  an outlet means for discharging a dialysate from the dialyzer membrane; and
  a heat pump coupled to the inlet means which is configured to exchange thermal energy between a heat reservoir and the dialysis fluid in the inlet means via a heat exchanger, wherein the heat reservoir is ambient air or dialysate in the outlet means.

2. The dialysis unit according to claim 1 wherein the heat pump is configured to utilize ambient air as the heat reservoir.

3. The dialysis unit according to claim 1, wherein the heat pump is further coupled to the outlet means, wherein the heat pump is configured to use the dialysate in the outlet means as the heat reservoir and to exchange thermal energy between the dialysate in the outlet means and the dialysis fluid in the inlet means via the heat exchanger.

4. The dialysis unit according to claim 1, wherein the heat pump is configured to transfer in a first operating mode thermal energy from the heat reservoir to the dialysis fluid in the inlet means so as to heat the dialysis fluid.

5. The dialysis unit according to claim 4, wherein the heat pump is configured to transfer in a second operating mode thermal energy from the dialysis fluid in the inlet means to the heat reservoir so as to cool the dialysis fluid.

6. The dialysis unit according to claim 1, further comprising in the inlet means an extra heating device coupled to the inlet means in the direction of flow between the heat pump and the dialyzer membrane, the extra heating device being configured to heat the dialysis fluid in the inlet means.

7. The dialysis unit according to claim 6, in which the extra heating device is an electrically operated heating.

8. The dialysis unit according to claim 1 further comprising a delivery pump arranged in the direction of flow between the heat pump and the dialyzer membrane.

9. The dialysis unit according to claim 1, further comprising a degassing device coupled to the inlet means which is configured to remove gases contained in the dialysis fluid.

10. The dialysis unit according to claim 9, wherein the degassing device is coupled to the inlet means in the direction of flow between the heat pump and the dialyzer membrane or in the direction of flow ahead of the heat pump.

11. The dialysis unit according to claim 1, further comprising a dialyzer having the dialyzer membrane, wherein the inlet means and the outlet means are coupled to the dialyzer, and wherein the dialyzer further includes an inlet port and an outlet port for an inflow and an outflow of blood to be purified by means of the dialysis unit.

12. The dialysis unit according to claim 1, wherein the inlet means is configured to supply the dialysis fluid to the dialyzer membrane; the outlet means is configured to discharge the dialysate from the dialyzer membrane; and the heat pump is configured to control temperature of the dialysis fluid supplied to the dialyzer membrane.

13. The dialysis unit according to claim 1, wherein the heat pump is configured to heat the dialysis fluid supplied to the dialyzer membrane in a first operating mode.

14. The dialysis unit according to claim 13, wherein the inlet means and the outlet means are configured to receive a cleaning fluid flowing through the inlet means and the outlet means to clean the inlet means and the outlet means and the dialysis unit is configured to be rinsed, such that when the dialysis unit is rinsed, the heat pump is configured in a second operating mode to cool a rinsing fluid or the dialysis fluid in the inlet means.

* * * * *